United States Patent
Gibson et al.

(10) Patent No.: US 7,902,308 B2
(45) Date of Patent: Mar. 8, 2011

(54) POLYMERISATION CATALYSTS

(75) Inventors: Vernon Charles Gibson, London (GB); Daniel Charles Howard Oakes, London (GB)

(73) Assignee: Ineos Europe Limited, Hampshire (GB)

( * ) Notice: Subject to any disclaimer, the term of this patent is extended or adjusted under 35 U.S.C. 154(b) by 362 days.

(21) Appl. No.: 11/991,089

(22) PCT Filed: Sep. 15, 2006

(86) PCT No.: PCT/GB2006/003430
§ 371 (c)(1),
(2), (4) Date: May 5, 2008

(87) PCT Pub. No.: WO2007/034149
PCT Pub. Date: Mar. 29, 2007

(65) Prior Publication Data
US 2009/0043061 A1 Feb. 12, 2009

(30) Foreign Application Priority Data
Sep. 20, 2005 (EP) .................... 05255794

(51) Int. Cl.
C08F 4/64 (2006.01)
C08F 4/72 (2006.01)
C08F 4/69 (2006.01)
C08F 4/52 (2006.01)

(52) U.S. Cl. ......... 526/161; 526/172; 526/134; 526/169; 526/169.2; 526/348; 526/348.2; 526/348.5; 526/348.6; 526/351; 526/352; 526/346; 526/344; 526/318; 526/335

(58) Field of Classification Search .......... 556/51, 556/57, 52; 526/172, 161, 348
See application file for complete search history.

(56) References Cited

U.S. PATENT DOCUMENTS
6,333,292 B1 * 12/2001 Gibson et al. .......... 502/167
6,593,266 B1 * 7/2003 Matsui et al. .......... 502/103
7,253,132 B2 * 8/2007 Nakayama et al. ........ 502/115

FOREIGN PATENT DOCUMENTS
EP 0 950 667 A2 10/1999
EP 0 953 571 A1 11/1999
WO WO 98/30609 7/1998
WO WO 99/19335 4/1999
WO WO 01/07491 A1 2/2001
WO WO 2004/037870 * 5/2004

OTHER PUBLICATIONS

Form PCT/IB/326, Int'l Preliminary Report on Patentability and Written Opinion of the Int'l Searching Authority, PCT International Application No. PCT/GB2006/003430; International Filing Date Sep. 15, 2006 (11 pgs).
Chemical Abstracts Service, Columbus, OH; Matsui, Shigekazu et al; "Transition metal compounds and catalysts and method for polymerization of olefins"; XP002370222 & JP 2000 086677, Mar. 28, 2000 (4 pgs).
Oakes, Daniel C.H., et al; "The surprisingly beneficial effect of soft donors on the performance of early transition metal olefin polymerisation catalysts"; Chemical Communications; pp. 2174-2175 (2004).

* cited by examiner

*Primary Examiner* — Rip A. Lee
(74) *Attorney, Agent, or Firm* — Nixon & Vanderhye

(57) ABSTRACT

A complex compound comprising the skeletal unit of Formula A,

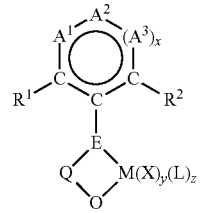

Formula A wherein the ring represented by $C(R^1)-A^1-A^2-(A^3)_x-C(R^2)—C—$ has delocalised unsaturation and is optionally substituted via one or more of $A^1$, $A^2$ and $A^3$ with atoms or groups selected from hydrogen, alkyl, aryl, halogen, or heterocyclic groups containing at least one N, S or O in a carbon ring; $A^1$, $A^2$ and $A^3$ are selected from carbon, nitrogen or oxygen, $R^1$ and $R^2$ are each selected from chlorine, bromine or iodine; x is zero or 1, O is oxygen, E is nitrogen, phosphorus or arsenic, Q represents a divalent bridging group comprising one or more Group 14 atoms; M is a metal selected from Groups 3 to 7; X represents a monovalent atom or group covalently or ionically bonded to M; L is a mono- or bidentate molecule datively bound to M, y satisfies the valency of M and z is from 0 to 5. The complex can be used to polymerise olefins optionally with organo-Al or -B compounds as activator.

30 Claims, No Drawings

POLYMERISATION CATALYSTS

This application is the U.S. National Phase of International Application PCT/GB2006/003430, filed 15 Sep. 2006, which designated the U.S. PCT/GB2006/003430 claims priority to European Application No. 05255794.9 filed 20 Sep. 2005. The entire content of these applications are incorporated herein by reference.

The present invention relates to transition metal-based polymerisation catalysts and to their use in the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last three decades, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent, or, in the case of propylene, in bulk.

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so-called "low density" polyethylene produced by the high pressure free radical catalysed polymerisation of ethylene. Such polymers and copolymers are used extensively in the manufacture of flexible blown film.

Polypropylenes are also commercially produced in a variety of different types and grades. Homopolymerisation of propylene with transition metal based catalysts leads to the production of grades with a wide variety of applications. Copolymers of propylene with ethylene or terpolymers with ethylene and higher 1-olefins are also useful materials.

In recent years the use of certain metallocene compounds as catalysts (for example biscyclopentadienylzirconiumdichloride activated with alumoxane) has provided potentially high activity in the polymerisation of olefins. Other derivatives of metallocenes have been shown to be potentially useful for producing polypropylene with good activity, molecular weight and tacticity control. However, metallocene catalysts of this type suffer from a number of disadvantages, for example, high sensitivity to impurities when used with commercially available monomers, diluents and process gas streams, the need to use large quantities of expensive alumoxanes to achieve high activity, difficulties in putting the catalyst on to a suitable support and synthetic difficulties in the production of more complex catalyst structures suitable for polymerising propylene in a tactic manner.

EP0950667 discloses a wide variety of non-metallocene transition metal-based complexes for use as catalysts in polymerising olefins. These transition metal catalysts can comprise, for example, the skeletal unit

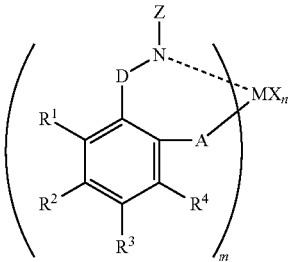

wherein M is a group 3 to 11 transition metal, m is an integer of 1 to 6, A is —O—, —S—, —Se— or —N—($R^5$)—, D is $C(R^7)(R^8)$, $Si(R^9)(R^{10})$ or the like, Z is —$R^{13}$ and —$R^{14}$, =$C(R^{15})R^{16}$, =$NR^{17}$ or the like, $R^1$ to $R^{17}$ are each H, a hydrocarbon group or the like, n is a number satisfying a valence of M; X is halogen, a hydrocarbon group or like. EP0950667 specifically discloses, amongst numerous formulae, a complex having the formula

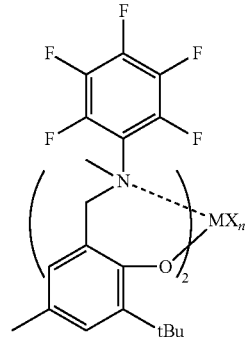

wherein X and M are as defined above.

An object of the present invention is to provide an improved transition metal complex which can be used, optionally with an activator, for polymerising unsaturated monomers. A further object of the present invention is to provide catalyst system and a process for polymerising monomers, for example, olefins, and especially for polymerising ethylene alone or propylene alone, or for copolymerising ethylene with higher 1-olefins with high activity. A further object is to provide a catalyst for copolymerising ethylene with a higher comonomer olefin which provides improved incorporation of the comonomer.

In its broadest aspect the present invention provides a transition metal complex compound comprising the skeletal unit depicted in Formula A Formula A

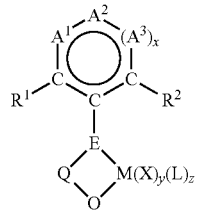

wherein the ring represented by C(R¹)-A¹-A²-(A³)ₓ-C(R²)—C— has delocalised unsaturation and is optionally substituted via one or more of A¹, A² and A³ with atoms or groups selected from hydrogen, alkyl, aryl, halogen, and heterocyclic groups containing at least one N, S or O in a carbon ring; A¹, A² and A³ are selected from carbon, nitrogen and oxygen; R¹ and R² are selected from hydrocarbyl, chlorine, bromine and iodine at least one of R¹ and R² being chlorine, bromine or iodine; x is zero or 1, O is oxygen, E is nitrogen, phosphorus or arsenic, Q represents a divalent bridging group comprising one or more Group 14 atoms; X represents a monovalent atom or group covalently or ionically bonded to M; L is a mono- or bidentate molecule datively bound to M, y satisfies the valency of M and z is from 0 to 5.

When R¹ or R² is hydrocarbyl, preferably it is selected for $C_1$ to $C_{20}$ alkyl and aryl each of which my be unsubstituted or substituted by a heteroatom or group, for example halogen or an S, O or N-containing group. Examples are methyl, ethyl, isopropyl, t-butyl and phenyl. Preferably R¹ and R² are both selected from chlorine, bromine and iodine, preferably chlorine or bromine, most preferably chlorine.

A¹, A² and A³ are preferably selected from carbon and nitrogen and are most preferably all carbon. In the ring represented by C(R¹)-A¹-A²-(A³)ₓ-C(R²)—C, x is preferably one, making the ring six membered. Preferably the ring is a benzene ring.

E is preferably nitrogen.

The divalent bridging group Q can be, for example, the simple divalent group C(R¹⁰)₂ or a polyalkylene chain [C(R¹⁰)₂]_q, a silane bridge [Si(R¹⁰)₂]_m, or a polyalkylene-silane bridge [C(R¹⁰)₂]_p[Si(R¹)₂]_m, wherein the R¹⁰ groups can be, for example, independently selected from hydrogen, hydrocarbyl, substituted hydrocarbyl, heterocarbyl and substituted heterocarbyl, m is one or more, preferably 1 to 20, p is one or more, preferably 1 to 20 and q is two or more preferably 2 to 20. Two or more of the R¹⁰ groups may connect together, for example, to form a carbocyclic or heterocyclic ring system within the bridging group Q. Specific examples of Q include methylene, dimethylmethylene, ethylene, propylene, dimethylpropylene, 1,1-dimethyl-3,3-dimethylpropylene or butylene; dimethylsilyl, methylphenylsilyl, tetramethyldisiloxane, 1,1,4,4-tetramethyldisilylethylene and dimethylgermanyl; or Q may be ortho, meta or para-phenylene Q preferably comprises a chain of at least 3 carbon atoms connecting E and O in Formula A. The said chain can be saturated or unsaturated and can, is desired be substituted by one or more hetero atoms, hetero-containing groups, hydrocarbon moieties or heterohydrocarbon moieties. Examples are halogen atoms, NR²⁰R²¹, =NR²², OR²³, methyl, ethyl, n-propyl, isopropyl, t-butyl, phenyl, benzyl, naphthyl, imidazoyl and pyridyl. R²⁰ to R²³ can be, for example $C_1$ to $C_{20}$ hydrocarbyl, preferably methyl, ethyl, isopropyl or tertiary-butyl. If desired the hydrocarbon moieties or heterohydrocarbon moieties can be joined to the said chain of carbon atoms via more than one bond. For example the chain can be fused to a benzene or pyridine moiety.

In the complex compound depicted in Formula A of the present invention the bridging group Q preferably comprises a saturated or unsaturated ring system, for example, a benzene, cyclohexene, cyclohexane, pyrazole, pyridine, piperidine, pyrazine, pyrimidine, or a thiazole ring system, or a polynuclear homocyclic or heterocyclic system such as, for example, naphthalene, quinoline or imidazole. For example, such a ring system may be a substituent on the divalent bridging group, or may be the bridging group itself or a part thereof. Thus for example, Q may comprise a benzene ring system. Such a benzene ring system may be present, for example, as a direct ortho-phenylene bridge between the oxygen and nitrogen atoms in formula A, or as an ortho-phenylene group in series with another atom or atoms in the bridge, or as a phenyl substituent to another atom in the bridge The metal M is a transition metal is selected from groups 3 to 11 or lanthanide, preferably groups 3 to 7. Preferred metals are those of Group IV, or scandium or yttrium. More preferred are Ti(IV), Ti(III), Ti(II), Zr(IV), Zr(III), Zr(II), Hf(IV), Hf(III), Hf(II), Sc(III) and Y(III).

L is preferably an ether, alcohol, amine, ester, phosphine, alkene, alkyne or arene, and in particular may be a diene.

A particularly preferred complex compound in accordance with the present invention comprises a skeletal unit of Formula B:

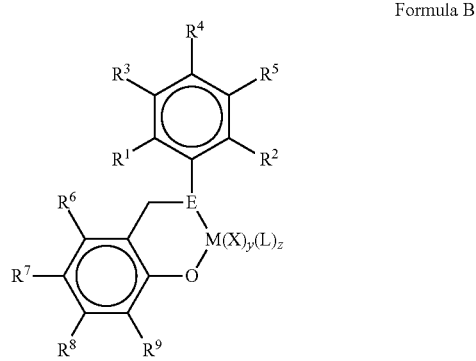

Formula B wherein R¹ and R² are selected from hydrocarbyl, chlorine, bromine and iodine at least one of R¹ and R² being chlorine, bromine or iodine, O is oxygen, E is nitrogen, phosphorus or arsenic; X represents a monovalent atom or group covalently or ionically bonded to M; L is a mono- or bidentate molecule datively bound to M, and n is from 0 to 5, R³ to R⁹ are independently selected from hydrogen and hydrocarbyl, hetero-substituted hydrocarbyl and heterocyclic groups containing 1 to 10 carbon atoms; y satisfies the valency of M and z is from 0 to 5.

Examples of the groups R³ to R⁹ are hydrogen, methyl, ethyl, n-propyl, n-butyl, n-hexyl, and n-octyl, methoxy, ethoxy, dimethylamino, phenyl and naphthyl.

Preferably z is zero, 1 or 2. E is preferably nitrogen.

The univalent radical X in the complex of Formula A and Formula B is preferably selected from $C_1$-$C_{10}$ alkyl, $C_6$-$C_{10}$ aryl, halide, hydride, hydrocarbyloxide, and amide. Examples of such groups are N,N-dimethylamido, N,N-diethylamido, chloro, bromo, methyl, ethyl, n-propyl, isopropyl, benzyl, n-butyl and n-octyl.

Examples of preferred novel compounds of the present invention are those compounds comprising the skeletal unit as depicted in Formula C:

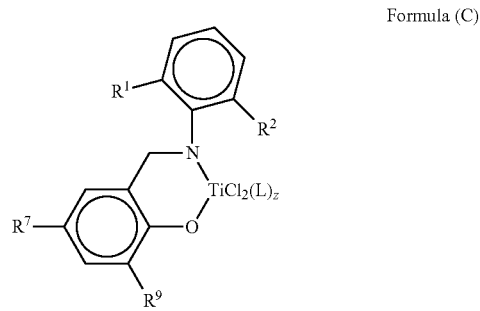

Formula (C)

wherein $R^1$ and $R^2$ are both chlorine or are both bromine, $R^7$ and $R^9$ are $C_1$ to $C_6$ alkyl, preferably tertiarybutyl, z is 1 or 2 and L is secondary amine, preferably dimethylamine.

The present invention further provides a catalyst for the polymerisation of 1-olefins comprising (1) the compound of Formula A, B or C above, and optionally (2) an activator.

The optional activator compound employed in the catalyst system of the present invention is suitably selected from organoaluminium compounds and organoboron compounds and may for example comprise a catalyst-activating support which is a solid particulate substance, insoluble in hydrocarbons, comprising at least magnesium and aluminium atoms and hydrocarbyloxy groups containing 1 to 20 carbons atoms. Catalysts activating supports of this type are further described later in this specification. Suitable organoaluminium compounds include trialkyl- or triaryl-aluminium compounds, for example, trimethylaluminium, triethylaluminium, tributylaluminium, tri-n-octylaluminium, ethylaluminium dichloride, diethylaluminium chloride, methylaluminium dichloride, dimethylaluminium chloride, tris(pentafluorophenyl)aluminium and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear, cyclic and cage compounds. The cyclic alumoxanes can be represented by the formula $[R^{16}AlO]_s$, and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable organoboron compounds are dimethylphenylammoniumtetra(phenyl)borate, trityltetra(phenyl)borate, triphenylboron, dimethylphenylammonium tetra(p-entafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl)boron. Mixtures of organoaluminium compounds and organoboron compounds may be used.

In the preparation of the catalysts of the present invention the quantity of activating compound selected from organoaluminium compounds and organoboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of M present in the compound of Formula A or B.

EP1238989 discloses the use of activators (Lewis acids) selected from
- (b-1) ionic-bonding compounds having a $CdCl_2$ type or a $CdI_2$ type of layered crystal structure;
- (b-2) clays, clay minerals, or ion-exchange layered compounds;
- (b-3) heteropoly-compounds; and
- (b-4) halogenated lanthanoid compounds.

The catalyst of the present invention can be activated in the manner of EP1238989 if desired. Such Lewis acids are those compounds which capable of receiving at least one electron pair and is capable of forming an ion pair by reaction with the transition metal complex. The Lewis acid includes the aforementioned (b-1) ionic-bonding compounds having a layered crystal structure of a $CdCl_2$ type or $CdI_2$ type (b-2) clay, clay minerals, or ion-exchange layered compounds, (b-3) heteropoly compounds, and (b-4) halogenated lanthanoid compounds. The Lewis acid further includes $SiO_2$, $Al_2O_3$, natural and synthetic zeolites which have Lewis acid points formed by heating or a like treatment, and complexes and mixtures thereof.

U.S. Pat. No. 6,399,535 discloses a coordinating catalyst system capable of polymerising olefins comprising:

(I) as a pre-catalyst, at least one non-metallocene, non-constrained geometry, bidentate ligand containing transition metal compound or tridentate ligand containing transition metal compound capable of (A) being activated upon contact with the catalyst support-activator agglomerate of (II) or (B) being converted, upon contact with an organometallic compound, to an intermediate capable of being activated upon contact with the catalyst support-activator agglomerate of (II), wherein the transition metal is at least one member selected from Groups 3 to 10 of the Periodic table; in intimate contact with (II) catalyst support-activator agglomerate comprising a composite of (A) at least one inorganic oxide component selected from $SiO_2$, $Al_2O_3$, MgO, $AlPO_4$, $TiO_2$, $ZrO_2$, and $Cr_2O_3$ and (B) at least one ion containing layered material having interspaces between the layers and sufficient Lewis acidity, when present within the catalyst support-activator agglomerate, to activate the pre-catalyst when the pre-catalyst is in contact with the catalyst support-activator agglomerate, said layered material having a cationic component and an anionic component, wherein said cationic component is present within the interspaces of the layered material, said layered material being intimately associated with said inorganic oxide component within the agglomerate in an amount sufficient to improve the activity of the coordinating catalyst system for polymerizing ethylene monomer, expressed as Kg of polyethylene per gram of catalyst system per hour, relative to the activity of a corresponding catalyst system employing the same pre-catalyst but in the absence of either Component A or B of the catalyst support-activator agglomerate; wherein the amounts of the pre-catalyst and catalyst support-activator agglomerate which are in intimate contact are sufficient to provide a ratio of micromoles of pre-catalyst to grams of catalyst support-activator agglomerate of from about 5:1 to about 500:1. The layered material can be, for example, a smectite clay. The catalyst of the present invention can be used with a catalyst support-activator agglomerate as described in U.S. Pat. No. 6,399,535 if desired.

The optional activator (b) of the present invention can comprise a catalyst-activating support which is a solid particulate substance, insoluble in hydrocarbons, comprising at least magnesium and aluminium atoms and hydrocarbyloxy groups containing 1 to 20 carbons atoms, the molar ratio of Mg/Al being in the range 1.0 to 300 and the molar ratio of hydrocarbyloxy groups to aluminium atoms being in the range 0.05 to 2.0, the average particle size of the support being in the range 3 to 80 micrometres (μm), Catalyst-activating hydrocarbon-insoluble supports of this type preferably contain a Mg/Al ratio in the range 40 to 150 and has a molar ratio of hydrocarbyloxy to Al in the range 0.2 to 2.0. They are preferably prepared by at least partially dissolving a magnesium halide, preferably magnesium dichloride, in an alcohol containing 1 to 20 carbons atoms and contacting the product with an organoaluminium compound having the formula $AlR_nX_{3-n}$ wherein X is halogen or hydrogen and n is 1 to 3. Supports of this type are disclosed in WO 2004/037870 and for details of their preparation this disclosure provides useful information. Examples of organoaluminium compounds that can be employed to make catalyst-activating hydrocarbon-insoluble supports are $R_3Al$, $R_2AlX$ and $RAlX_2$ wherein R is preferably $C_1$ to $C_{20}$ hydrocarbyl, and X is chlorine or bromine, preferably chlorine. R is preferably selected from methyl, ethyl, propyl, isopropyl, n-butyl, sec-butyl, tert butyl, n-pentyl, n-hexyl, n-octyl and n-decyl. Examples of alcohols that can be employed to make catalyst-activating hydrocarbon-insoluble supports are $R^1OH$ wherein $R^1$ is aliphatic, alicyclic or aralkyl, for example, methyl, ethyl, propyl, isopropyl, n-butyl, sec-butyl, tert butyl, n-pentyl, n-hexyl, n-octyl, n-decyl, cyclohexyl, ethylcyclohexyl and benzyl. In the preparation of such supports, the magnesium halide is preferably dissolved completely in the alcohol, heating or refluxing the mixture if necessary. Any undissolved magnesium halide is preferably separated before reacting the solution with the organoaluminium compound. Reacting the solution with the organoaluminium compound using quantities having the afore-recited Mg/Al ratios produces a solid having the desired chemical characteristics. The particle size of the product can be adjusted if desired by conventional methods, for examples, milling, sieving, pressing and the like. The catalyst-activating hydrocarbon-insoluble support and its preparation are suitably protected to exclude air and moisture. Preferably the preparation and storage are in an inert gas atmosphere.

In addition to the activator compound, it can be advantageous to employ catalytic quantities of certain halogenated compounds that are capable of promoting catalyst activity. Promotors of this type are especially useful in the case that the transition metal in the complex is vanadium. U.S. Pat. No. 5,191,042 discloses that certain vanadium-based catalysts activated with organoaluminium compounds can be promoted using a variety of halogenated organic compounds, for example, carbon tetrachloride, hexachloroethylene, benzylbromide, benzylchloride and 2,3- or 1,3-dichloropropylene. Other examples of halogenated organic compounds that can be used in this manner are ethyl trichloroacetate, chloroform ($CHCl_3$) and n-butylchloride. U.S. Pat. No. 5,191,042 also refers to the disclosure of Cooper (T. A Cooper, Journ. Am. Chem. Soc., 4158 (1973), which defines in Table 1 an organic halide activity index based on the ability of the halide to oxidize certain vanadium compounds under standard conditions. For example, carbon tetrachloride is assigned a reactivity of 1 in tetrahydrofuran at 20° C., and other listed halogenated organic compounds have reactivities of from about 0.02 to greater than 200 relative to carbon tetrachloride. When it is desired to use a halogenated promotor, it is preferred to use those having a Cooper Index ranging from about 0.01 up to about 30. The use of such promoters, especially in combination with vanadium-based catalysts is generally well known in the art, and for details of use of the such promoters reference may be made to U.S. Pat. No. 5,191,042 and to other prior art in this field. In the present invention it is possible to employ any halogenated organic compound as a promoter, but the compounds mentioned above are preferred.

The catalyst of the present invention can, if desired, be utilised on a conventional support material. Suitable support materials are, for example, silica, alumina, or zirconia, magnesia, magnesium chloride or a polymer or prepolymer, for example polyethylene, polystyrene, or poly(aminostyrene).

The catalyst or catalyst system of the present invention can if desired comprise more than one of the defined transition metal compounds.

In addition to said one or more defined transition metal compounds, the catalyst or catalyst system of the present invention can also include one or more other types of transition metal compounds or catalysts, for example, transition metal compounds of the type used in conventional Ziegler-Natta catalyst systems, metallocene-based catalysts, or heat activated supported chromium oxide catalysts. The catalyst or catalyst system of the present invention can also used in conjunction with other catalysts producing only 1-olefins, either inside or outside the polymerisation reactor, and in this way make copolymers of ethylene or propylene and these 1-olefins. Suitable catalysts for producing 1-olefins may produce only 1-butene, only 1-hexene or a distribution (for example, a Schulz-Flory distribution) of 1-olefins.

If desired, the catalyst or catalyst system can be formed in situ in the presence of the support material, or the support material can be pre-impregnated or premixed, simultaneously or sequentially, with one or more of the catalyst components. The catalyst and catalyst system of the present invention can if desired be supported on a heterogeneous catalyst, for example, a magnesium halide supported Ziegler Natta catalyst, a chromium oxide type supported catalyst (eg a heat activated chromium oxide supported on silica) or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, cycloolefins or dienes comprising contacting the monomeric olefin under polymerisation conditions with the polymerisation catalyst of the present invention.

Suitable monomers for use in making homopolymers using the polymerisation process of the of the present invention are, for example, ethylene, propylene, butene, hexene, and styrene. Preferred monomers are ethylene and propylene.

Suitable monomers for use in making copolymers using the polymerisation process of the present invention are ethylene, propylene, 1-butene, 1-hexene, 4-methylpentene-1,1-octene, methyl methacrylate, methyl acrylate, butyl acrylate, acrylonitrile, vinyl acetate, vinyl chloride, styrene and dienes, such as butadiene or hexadiene and cycloolefins, such as norbornene.

A particularly preferred process in accordance with the present invention is the copolymerisation of ethylene and or propylene with comonomers selected from 1-olefins, acrylic acid esters, vinyl esters and vinyl aromatic compounds. Examples of suitable comonomers are 1-butene, 1-hexene, 4-methylpentene-1, methyl methacrylate, methyl acrylate, butyl acrylate, acrylonitrile, vinyl acetate, and styrene.

Preferred polymerisation processes are the homopolymerisation of ethylene or the homopolymerisation of propylene or copolymerisation of ethylene with one or more of propylene, butene, hexane-1 and 4-methylpentene-1.

Also preferred is a process for the copolymerisation of ethylene and or propylene with comonomers selected from 1-butene, 1-hexene, 4-methylpentene-1, methyl methacrylate, methyl acrylate, butyl acrylate, acrylonitrile, vinyl acetate, and styrene, diene, cyclic olefin, norbornene and substituted norbornene.

The polymerisation conditions can be, for example, bulk phase, solution phase, slurry phase or gas phase. If desired, the catalyst can be used to polymerise ethylene under high pressure/high temperature process conditions wherein the polymeric material forms as a melt in supercritical ethylene.

Preferably the polymerisation is conducted under gas phase fluidised or stirred bed conditions.

Slurry phase polymerisation conditions or gas phase polymerisation conditions are particularly useful for the production of high-density grades of polyethylene. In these processes the polymerisation conditions can be batch, continuous or semi-continuous. In the slurry phase process and the gas phase process, the catalyst is generally fed to the polymerisation zone in the form of a particulate solid. This solid can be, for example, an undiluted solid catalyst system formed from the complex of Formula A or B and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymerisation is supported on a support material. Most preferably the catalyst system is supported on a support material prior to its introduction into the polymerisation zone. Suitable support materials are, for example, magnesium chloride, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

A problem that can occur in the gas and slurry phase polymerisation of olefins is that of fouling of the reactor walls, any stirrer that may be present and spalling or agglomeration of the polymer due, for example, to the presence of static electricity. The problem can be reduced or eliminated by judicious use of suitable antistatic agents. One example of a family of antistatic agents suitable for use in the polymerisation of olefins are commercially available under the trade name "STADIS".

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the polymerisation process of the present invention the process conditions are preferably gas phase fluidised or stirred bed polymerisation conditions.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

More generally, for gas phase, solution phase or slurry phase polymerisation processes, the catalyst or catalysts of the present invention can be employed, if desired, using processes analogous to those disclosed in WO02/46246 and U.S. Pat. No. 6,605,675. For example, a catalyst component slurry and a catalyst component solution can be combined before or during introduction into the polymerisation reactor. The properties of polymers produced using such methods can be advantageously controlled thereby. The catalysts of the present invention can also be employed in the process disclosed in U.S. Pat. No. 6,610,799. In this process, mixtures of two or more supported catalysts can be utilised containing differing amounts of catalyst components wherein the concentrations of the individual catalyst components can be independently controlled within the polymerisation reactor.

The catalyst of the present invention can be used in conventional commercial polymerisation facilities and its use can be sandwiched between production runs using other commercial catalyst systems of the supported or unsupported type, eg, using Ziegler Natta catalysts, metallocene catalysts, heat activated chromium oxide catalysts and late transition metal catalyst systems. Transitioning between catalyst systems of these types has been extensively described in the prior art and reference may be made to the prior art methods for analogously suitable methods readily adaptable to use of the catalyst of the present invention. For example, see EP 751965, U.S. Pat. Nos. 5,442,019, 5,672,665, 5,747,612, 5,753,786, EP 830393, U.S. Pat. No. 5,672,666, EP1171486, EP885247, EP1182216, U.S. Pat. No. 6,284,849. US2004/0127655, WO04/060938, US2004/0138391, WO, 04/060921, WO04/060922, WO04/060929, WO04/060930, and WO04/060931.

The invention is further illustrated with reference to the following Examples. In the Examples all manipulations of air/moisture-sensitive materials were performed on a conventional vacuum/inert atmosphere (nitrogen) line using standard Schlenk line techniques, or in an inert atmosphere glove box.

EXAMPLE 1

Comparative

Synthesis of (i) 2,4-bis(tert-butyl)-6-[[(2,6-dimethylphenyl)amino]methyl]-phenol (Compound 1) and the Titaniumchloride Complex Thereof This compound and the titanium complex was synthesised using the procedure reported by D. C. H. Oakes, B. S. Kimberley, V. C. Gibson, D. J. Jones, A. J. P. White and D. J. Williams in *Chem. Commun.*, 2004, 2174.

EXAMPLE 2

Invention 2.1—Synthesis of 2,4-bis(tert-butyl)-6-[[(2,6-dibromophenyl)imino]methyl]phenol To a stirred solution of 3,5-di-tert-butyl-2-hydroxybenzaldehyde (0.5 g, 2.1 mmol) in toluene (20 ml) was added 2,6-dibromoroaniline (0.93 g, 3.7 mmol), and p-tolyl sulfonic acid (0.4 g, 2.1 mmol). The reaction mixture was heated to 90° C. for 24 hours. The red-brown solution was allowed to cool and the solvent was removed under reduced pressure leaving a red solid. $Et_2O$ (20 ml) was added, and the solution was washed with $Na_2SO_4$ (aq) solution (3×100 ml). The organic fraction was separated, dried ($MgSO_4$), and the solvent removed under reduced pressure. The yellow solid was purified by recrystallisation from hot ethanol affording the product as yellow crystals. Yield 0.7 g, 71%.
Analysis $^1$H NMR (250 MHz, $CDCl_3$): δ12.74 (s (br), 1H, OH), δ8.47 (s, 1H, HC=N), δ7.61 (d, 2H, $^3J_{HH}$=8.0 Hz, ArH), δ7.53 (d, 1H, $^4J_{HH}$=2.4 Hz, ArH), δ7.21 (d, 1H, $^4J_{HH}$=2.4 Hz, ArH), δ6.91 (t, 1H, $^3J_{HH}$=8.0 Hz, ArH), δ1.50 (s, 9H, $C(CH_3)_3$), δ1.34 (s, 9H, $C(CH_3)_3$). $^{13}C$ {$^1H$} NMR (62.90 MHz, $CDCl_3$): δ170.60, 158.67, 146.95, 140.71, 137.28, 132.37, 129.23, 127.35, 126.85, 117.25, 116.43, 35.18 ($C(CH_3)_3$), 34.20 ($C(CH_3)_3$), 31.44 ($C(CH_3)_3$), 29.44 ($C(CH_3)_3$). $C_{21}H_{25}Br_2NO$ (467.24) Calculated (found): C, 53.98; (54.14), H, 5.39; (5.49), N, 3.00; (2.80). MS (EI) (467.24): 467 (M+).

2.2—Synthesis of 2,4-bis(tert-butyl)-6-[[(2,6-dibromophenyl)amino]methyl]phenol (Compound 2)

To a suspension of 2,4-bis(tert-butyl)-6-[[(2,6-dibromophenyl)imino]methyl]phenol (0.91 g, 2.41 mmol) in methanol (20 ml) was added $NaBH_4$ (1.2 g), in small portions. The yellow suspension was stirred for 2 hours during which the yellow solution turned clear. Water (10 ml) was then slowly added, the organic phase separated and the aqueous phase extracted with dichloromethane (3×10 ml). The organic fractions were combined, dried ($NaSO_4$), and the solvent removed under reduced pressure. The crude product was purified by recrystallisation from hot hexane to afford the product as large colourless crystals. Yield 0.48 g, 95%.
Analysis $^1$H NMR (250 MHz, $CDCl_3$): δ8.89 (s, 1H, OH), δ7.57 (d, 2H, $^3J_{HH}$=8.0 Hz, ArH), δ7.33 (d, 1H, $^3J_{HH}$=2.4 Hz, ArH), δ7.00 (d, 1H, $^3J_{HH}$=2.3 Hz, ArH), δ4.46 (t, 1H, $^3J_{HH}$=8.0 Hz, ArH), δ4.29 (d, 2H, $^3J_{HH}$=8.0 Hz, $CH_2N$), δ4.08 (s (br), 1H, NH), δ1.47 (s, 9H, $C(CH_3)_3$), δ1.32 (s, 9H, $C(CH_3)_3$). $^{13}C$ {$^1H$} NMR (62.90 MHz, $CDCl_3$): δ153.92, 143.51, 141.14, 136.36, 132.75, 126.83, 124.04, 123.88, 121.63, 120.28, 52.27 ($CH_2N$), 35.07 ($C(CH_3)_3$), 34.21 ($C(CH_3)_3$), 31.64 ($C(CH_3)_3$), 29.66 ($C(CH_3)_3$), $C_{21}H_{27}Br_2NO$ (469.25) Calculated (found): C, 53.75; (53.83), H, 5.80; (5.73), N, 2.98; (2.89). MS (EI) (469.25): 469 (M+).

2.3 Synthesis of Titanium Complex(Complex 2)

To a cooled (0° C.) solution of $TiCl_2(NMe_2)_2$ (118.0 mg, 0.57 mmol) in toluene (20 ml), was added dropwise over 20 mins a solution of 2,4-bis(tert-butyl)-6-[[(2,6-dibromophenyl)amino]methyl]phenol (267.0 mg, 0.57 mmol) in toluene. The reaction mixture was allowed to warm to room temperature and stirred for a further 2 hours. The solvent was then removed in vacuo. and the residues washed with pentane (5.0 ml) and dried in vacuo. leaving the product as an orange solid. Yield 0.31 g, 81%.
Analysis $^1$H NMR (250 MHz, $CDCl_3$): δ 7.46 (d, 1H, $^3J_{HH}$=2.4 Hz ArH), δ 7.27 (d, 2H, $^4J_{HH}$=8.0 Hz ArH), δ 6.98 (d, 1H, $4J_{HH}$=2.4 Hz ArH), δ 6.29 (t, 1H, $^3J_{HH}$=8.0 Hz ArH), δ 4.66 (s, 2H, $CH_2N$), δ 4.24 (sept, 2H, $^3J_{HH}$=6.2 Hz, $NH(CH_3)_2$), δ 2.75 (d, 6H, $^3J_{HH}$=5.9 Hz, $NH(CH_3)_2$), δ 2.15 (d, 6H, $^3J_{HH}$=5.9 Hz, $NH(CH_3)_2$), δ 1.76 (s, 9H, $C(CH_3)_3$), δ 1.26 (s, 9H, $C(CH_3)_3$). $^{13}C$ {$^1H$} NMR (62.90 MHz, $CDCl_3$): δ 158.48, 155.22, 145.23, 136.30, 133.39, 132.38, 128.31, 127.22, 122.74, 121.08, 62.08 ($CH_2N$), 44.24 ($NH(CH_3)_2$), 42.06 ($NH(CH_3)_2$), 35.50 ($C(CH_3)_3$), 34.72 ($C(CH_3)_3$), 31.69 ($C(CH_3)_3$), 31.08 ($C(CH_3)_3$). $C_{25}H_{39}Br_2Cl_2N_3OTi$ (676.18) Calculated (found); C, 44.41; (44.69), H, 5.81; (5.93), N, 6.21; (6.14). MS (CI-ve) (676.18); 548 (M+—Cl($HNMe_2$)$_2$).

EXAMPLE 3

Invention 3.1—Synthesis of 2,4-bis(tert-butyl)-6-[[(2,6-dichlorophenyl)imino]methyl]phenol An analogous procedure was employed to that described above for the synthesis of 2,4-bis(tert-butyl)-6-[[(2,6-dibromophenyl)imino]methyl]phenol, using 2,6-dichloroaniline (1.03 g, 6.4 mmol) and 3,5-di-tert-butyl-2-hydroxybenzaldehyde (1.5 g, 6.4 mmol). The product was purified by recrystallisation from hot ethanol and the product isolated as yellow crystals. Yield 1.87 g, 77%.

Analysis $^1$H NMR (250 MHz, CDCl$_3$): δ12.85 (s, 1H, OH), δ8.56 (s, 1H, HC=N), δ7.54 (d, 1H, $^4J_{HH}$=2.6 Hz, ArH), δ7.38 (d, 2H, $^3J_{HH}$=8.0 Hz, ArH), δ7.21 (d, 1H, $^4J_{HH}$=2.6 Hz, ArH), δ7.05 (t, 1H, $^3J_{HH}$=8.0 Hz, ArH), δ1.50 (s, 9H, C(CH$_3$)$_3$), δ1.34 (s, 9H, C(CH$_3$)$_3$). $^{13}$C {$^1$H} NMR (62.90 MHz, CDCl$_3$): δ170.65 (HC=N), 158.68, 144.50, 140.74, 137.35, 129.17, 128.56, 127.41, 127.32, 125.86, 117.48, 35.18 (C(CH$_3$)$_3$), 34.19 (C(CH$_3$)$_3$), 31.43 (C(CH$_3$)$_3$), 29.46 (C(CH$_3$)$_3$), C$_{21}$H$_{25}$Cl$_2$NO (377.33) Calculated (found): C, 66.67; (66.61), H, 6.66; (6.57), N, 3.70; (3.64). MS (EI) (377.3): 377 (M+).

3.2—Synthesis of 2,4-bis(tert-butyl)-6-[[(2,6-dichlorophenyl)amino]methyl]-phenol Using an analogous procedure to the synthesis of 2,4-bis(tert-butyl)-6-[[(2,6-dibromophenyl)amino]methyl]phenol described above, NaBH$_4$ (0.8 g) was added to a solution of 2,4-bis(tert-butyl)-6-[[(2,6-dichlorophenyl)imino]methyl]phenol (0.91 g, 2.41 mmol). The product was purified from hot hexane and isolated as colourless crystals. Yield 0.61 g, 67%.

Analysis $^1$H NMR (250 MHz, CDCl$_3$): δ8.92 (s, 1H, OH), δ7.36 (d, 2H, $^3J_{HH}$=8.0 Hz, ArH), δ7.34 (d, 1H, $^4J_{HH}$=1.5 Hz, ArH), δ7.04 (t, 1H, $^3J_{HH}$=7.7 Hz, ArH), δ7.00 (d, 1H, $^4J_{HH}$=2.1 Hz, ArH), δ4.33 (d, 2H, $^3J_{HH}$=7.5 Hz, CH$_2$N), δ4.17-4.11 (m, 1H, NH), δ1.48 (s, 9H, C(CH$_3$)$_3$), δ1.33 (s, 9H, C(CH$_3$)$_3$). $^{13}$C {$^1$H} NMR (62.90 MHz, CDCl$_3$): δ153.93, 141.35, 141.20, 136.46, 129.99, 128.81, 125.37, 124.03, 123.83, 121.81, 51.96 (CH$_2$N), 35.08 (C(CH$_3$)$_3$), 34.22 (C(CH$_3$)$_3$), 31.66 (C(CH$_3$)$_3$), 29.72 (C(CH$_3$)$_3$), C$_{21}$H$_{27}$Cl$_2$NO (380.35) Calculated (found): C, 66.31; (66.29), H, 7.16; (7.08), N, 3.68; (3.59). MS (EI) (380.35): 380 (M+).

3.3—Synthesis of Titanium Complex(Complex 3)

Using a procedure analogous to that described for the synthesis of Complex 2 above, 2,4-bis(tert-butyl)-6-[[(2,6-dichlorophenyl)amino]methyl]phenol (310.6 mg, 0.81 mmol) was added to TiCl$_2$(NMe$_2$)$_2$ (169.3 mg, 0.81 mmol). The product was isolated an orange-red solid. Yield 0.46 g, 96%.

Analysis $^1$H NMR (250 MHz, C$_6$D$_6$): δ7.45 (d, 1H, $^4J_{HH}$=2.4 Hz ArH), δ7.06 (d, 2H, $^3J_{HH}$=8.0 Hz ArH), δ6.96 (d, 1H, $^4J_{HH}$=2.4 Hz, ArH), δ6.47 (t, 1H, $^3J_{HH}$=8.0 Hz ArH), δ4.62 (s, 2H, CH$_2$N), δ4.15 (sept, 2H, $^3J_{HH}$=6.0 Hz, 2(NH(CH$_3$)$_2$), δ2.69 (d, 6H, $^2J_{HH}$=6.0 Hz, NH(CH$_3$)$_2$), δ2.12 (d, 6H, $^2J_{HH}$=6.0 Hz, NH(CH$_3$)$_2$), δ1.74 (s, 9H, C(CH$_3$)$_3$), δ1.26 (s, 9H, C(CH$_3$)$_3$). $^{13}$C {$^1$H} NMR (62.90 MHz, C$_6$D$_6$); δ156.53, 155.12, 145.23, 136.46, 132.17, 130.68, 129.55, 128.27, 126.37, 122.64, 61.92 (CH$_2$N), 44.04 (NH(CH$_3$)$_2$), 41.77 (NH(CH$_3$)$_2$), 35.50 (C(CH$_3$)$_3$), 34.72 (C(CH$_3$)$_3$), 31.69 (C(CH$_3$)$_3$), 30.84 (C(CH$_3$)$_3$). C$_{25}$H$_{39}$Cl$_4$N$_3$OTi (587.27) Calculated (found); C, 51.13; (50.86), H, 6.69; (6.71), N, 7.16; (7.16). MS (CI-ve) (587.2); 497 (M+−(HNMe$_2$)$_2$).

EXAMPLE 4

Comparative

4.1—Synthesis of 2,4-bis(tert-butyl)-6-[[(2,3,4,5,6-pentafluorophenyl) imino]methyl]phenol Employing an analogous procedure to that described above for the synthesis of 2,4-bis(tert-butyl)-6-[[(2,6-dibromophenyl)imino]methyl]phenol, 2,3,4,5,6-pentafluoroaniline (0.54 g, 2.9 mmol) was added to 3,5-di-tert-butyl-2-hydroxybenzaldehyde (0.70 g, 2.9 mmol). The product was purified by recrystallisation from hot MeOH and isolated as yellow crystals.

Yield 0.59 g, 50%.

Analysis $^1$H NMR (250 MHz, CDCl$_3$): δ12.75 (s, 1H, OH), δ8.83 (s, 1H, HC=N), δ7.56 (d, 1H, $^4J_{HH}$=2.4 Hz, ArH), δ7.22 (d, 1H, $^4J_{HH}$=2.4 Hz, ArH), δ1.48 (s, 9H, C(CH$_3$)$_3$), δ1.34 (s, 9H, C(CH$_3$)$_3$). $^{13}$C {$^1$H} NMR (62.90 MHz, CDCl$_3$): δ171.71 (2 signals), 161.42, 158.82, 141.19, 137.59, 130.06 (2 signals), 127.62 (2 signals), 117.83, 35.15 (C(CH$_3$)$_3$), 34.19 (C(CH$_3$)$_3$), 31.34 (C(CH$_3$)$_3$), 29.34 (C(CH$_3$)$_3$). $^{19}$F {$^1$H} NMR (235.36 MHz, CDCl$_3$): δ−156.40, −163.11, −166.77. C$_{21}$H$_{22}$F$_5$NO (399.40) Calculated. (found): C, 63.15; (63.15), H, 5.55; (5.63), N, 3.51; (3.48). MS (EI) (399.4): 399 (M+).

4.2—Synthesis of 2,4-bis(tert-butyl)-6-[[(2,3,4,5,6-pentafluorophenyl)amino]methyl]phenol—Compound (4)

Using an analogous procedure to the synthesis of 2,4-bis(tert-butyl)-6-[[(2,6-dibromophenyl)amino]methyl]phenol described above, NaBH$_4$ (1.2 g) was added to a solution of 2,4-bis(tert-butyl)-6-[[(2,3,4,5,6-pentafluorophenyl)imino]methyl]phenol (0.5 g, 1.25 mmol). The product was isolated as an air sensitive white solid, and stored under nitrogen. Yield 0.48 g, 95%.

Analysis $^1$H NMR (250 MHz, CDCl$_3$): (OH/NH not observed) δ7.19 (d, 1H, $^4J_{HH}$=2.4 Hz, ArH), 67.00 (d, 1H, $^4J_{HH}$=2.4 Hz, ArH), δ4.41 (s, 2H, CH$_2$N), δ1.38 (s, 9H, C(CH$_3$)$_3$), δ1.22 (s, 9H, C(CH$_3$)$_3$). $^{13}$C {$^1$H} NMR (250 MHz, CDCl$_3$): δ152.88, 142.98, 142.03 (CF), 140.49 (CF), 139.63 (CF), 139.63 (CF), 138.36, 138.02 (CF), 136.90 (CF), 134.48 (CF), 126.45, 125.00, 124.08, 64.88 (CH$_2$N), 35.92, 35.03, 32.00, 30.33. $^{19}$F {$^1$H} NMR (235.36 MHz, CDCl$_3$): δ−159.7 (d, 2F, $^3J_{FF}$=19.5 Hz, o-F), δ−169.57 (t, 2F, $^3J_{FF}$=20.2 Hz, m-F), δ−174.64 (t, 1F, $^3J_{FF}$=21.6 Hz, p-F). C$_{21}$H$_{24}$F$_5$NO (401.41) Calculated (found); C, 62.83 (63.13), H, 6.03 (6.15), N, 3.49; (3.52). MS (EI) (401.41): 401 (M+).

4.3—Synthesis of Titanium Complex(Complex 4)

To a solid sample of 2,4-bis(tert-butyl)-6-[[(2,3,4,5,6-pentafluorophenyl)amino]methyl]-phenol (218.6 mg, 0.54 mmol) was rapidly added a solution of TiCl$_2$(NMe$_2$)$_2$ (112.6 mg, 0.54 mmol) in benzene at room temperature. The red solution was stirred for 1 hour, filtered, and the solvent then removed in vacuo to leave the crude product as a red residue. After extraction with pentane (15 ml), the mother liquor was filtered from the residue and cooled to −35° C. for 12 hours. The resulting solids were isolated by filtration while cold and dried in vacuo to leave the product as a red solid. Yield 0.24 g, 72%.

Analysis $^1$H NMR (500 MHz CDCl$_3$): δ7.28 (d, 1H, $^3J_{HH}$=2.4 Hz ArH), δ7.05 (d, 1H, $^3J_{HH}$=2.4 Hz ArH), δ4.82 (s, 2H, CH$_2$N), δ3.68 (sept, 2H, $^3J_{HH}$=5.9 Hz, 2(NH(CH$_3$)$_2$), δ2.72 (d, 6H, $^2J_{HH}$=6.1 Hz, NH(CH$_3$)$_2$), δ2.57 (d, 6H, $^2J_{HH}$=6.1 Hz, NH(CH$_3$)$_2$), δ1.57 (s, 9H, C(CH$_3$)$_3$), δ1.30 (s, 9H, C(CH$_3$)$_3$). $^{13}$C {$^1$H} NMR (125.80 MHz, CDCl$_3$): 154.61, 146.15, 141.57 (d, C—F$_o$ $^1J_{CF}$=237.6 Hz), 138.57 (d, C—F$_p$ $^1J_{CF}$=251.8 Hz), 137.99 (d, C—F$_m$ $^1J_{CF}$=235.2 Hz), 136.03, 130.71, 122.73, 122.16, 64.35 (CH$_2$N), 43.33 (NH(CH$_3$)$_2$), 42.77 (NH(CH$_3$)$_2$), 35.18 (C(CH$_3$)$_3$), 34.68 (C(CH$_3$)$_3$), 31.47 (C(CH$_3$)$_3$), 30.06 (C(CH$_3$)$_3$). $^{19}$F NMR (235.36 MHz CDCl$_3$): δ–150.09 (d, $^3J_{FF}$=24.0 Hz, o-F), –159.05 (t, $^3J_{FF}$=21.7 Hz p-F), –161.72 (dd, m-F). C$_{25}$H$_{36}$Cl$_2$F$_5$N$_3$OTi (608.34) Calculated (found): C, 49.36; (49.44), H, 5.96; (6.13), N, 6.91; (6.71). MS (CI-ve) (608.3): 401.

Polymerisation Using Complexes 1-4

Polymerisation tests were carried out in a 500 ml Fischer Porter polymerisation vessel equipped with an overhead mechanical stirrer, thermocouple, catalyst injection port, and gas line injection manifold. The polymerisation stirrer head was flame dried and then assembled under nitrogen in a glove box. Solvent (heptane—200 ml) was introduced via the gas line inlet direct from a solvent drying tower. Methylaluminoxane (4.0 mmol supplied by Aldrich) and, when required, co-monomer were introduced via syringe prior to the addition of precatalyst (ie titanium complex). All precatalysts were generated in situ by the addition of the desired ligand to a solution of TiCl$_2$(NMe$_2$)$_2$ in toluene and injected into the Fischer porter vessel immediately. Polymerisation was initiated by introducing ethylene gas at the required pressure to the stirred catalyst solution. The polymerisation runs were carried out for 30 minutes at 25° C. and were terminated by venting the vessel of ethylene and addition of MeOH/HCl (aq) solution. The isolated polymer products were recovered by filtration, washed with MeOH (20 ml) and dried to constant weight in a vacuum oven at 50° C. The results are shown in Table 1 from which it can be seen that Runs 4 to 14, which are all in accordance with the present invention, have provided very high catalyst activity. The Comparative Examples (1 and 4) are illustrated in Runs 1 to 3 and 15 to 17. These have given relatively low catalyst activities.

TABLE 1

| Run | Complex (μmol) | Pressure (bar) | Yield (g) | Activity (g mmol$^{-1}$bar$^{-1}$h$^{-1}$) |
|---|---|---|---|---|
| 1 | 1-(5.0) | 1 | 0.17 | 70$^c$ |
| 2 | 1-(5.0) | 4 | 0.72 | 72$^c$ |
| 3$^b$ | 1-(5.0) | 4 | 0.68 | 68$^c$ |
| 4 | 2-(0.2) | 1 | 0.16 | 1600$^c$ |
| 5 | 2-(0.5) | 4 | 1.37 | 1370$^c$ |
| 6$^b$ | 2-(0.5) | 4 | 0.95 | 950$^d$ |
| 7 | 3-(1.0) | 1 | 3.10 | 6200$^c$ |
| 8 | 3-(1.0) | 4 | 7.65 | 3825$^c$ |
| 9 | 3-(0.5) | 4 | 7.60 | 7600$^c$ |
| 10 | 3-(0.2) | 4 | 4.85 | 12130$^e$ |
| 11 | 3-(0.2) | 3 | 3.85 | 12830 |
| 12 | 3-(0.2) | 2 | 1.79 | 8950$^c$ |
| 13 | 3-(0.2) | 1 | 1.02 | 10200$^c$ |
| 14$^b$ | 3-(1.0) | 4 | 14.21 | 7110$^e$ |
| 15 | 4-(10.0) | 1 | 0.25 | 50$^c$ |
| 16 | 4-(10.0) | 4 | 0.80 | 40$^c$ |
| 17$^b$ | 4-(10.0) | 4 | 0.40 | 20$^c$ |

Notes on Table 1:
1. $^b$1-hexene comonomer (20 ml) was copolymerised with the ethylene.
2. $^c$M$_w$ = above 2 × 10$^6$
3. $^d$M$_n$ = 708000, M$_n$ = 253300, PDI = 2.8
4. $^e$M$_w$ = 475200, M$_n$ 159100, PDI = 2.9,

The invention claimed is:

1. A complex comprising the skeletal unit of Formula A

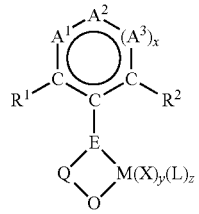

Formula A wherein the ring represented by C(R$^1$)-A$^1$-A$^2$-(A$^3$)$_x$-C(R$^2$)—C— has delocalized unsaturation and is optionally substituted via one or more of A$^1$, A$^2$ and A$^3$ with atoms or groups selected from hydrogen, alkyl, aryl, halogen, or heterocyclic groups containing at least one N, S or O in a carbon ring; A$^1$, A$^2$ and A$^3$ are selected from carbon, nitrogen or oxygen, R$^1$ and R$^2$ are each selected from chlorine, bromine or iodine; x is zero or 1, O is oxygen, E is nitrogen, phosphorus or arsenic, Q represents a divalent bridging group comprising one or more Group 14 atoms; M is a metal selected from Groups 3 to 7; X represents a monovalent atom or group covalently or ionically bonded to M; L is a mono- or bidentate molecule datively bound to M, y satisfies the valency of M and z is from 0 to 5.

2. A complex as claimed in claim 1 wherein R$^1$ and R$^2$ are both chlorine.

3. A complex as claimed in claim 1 wherein A$^1$, A$^2$ and A$^3$ are selected from carbon or nitrogen.

4. A complex as claimed in claim 1 wherein A$^1$, A$^2$ and A$^3$ are all carbon.

5. A complex as claimed in claim 1 wherein the ring represented by C(R$^1$)-A$^1$-A$^2$-(A$^3$)$_x$-C(R$^2$)—C is six membered.

6. A complex as claimed in claim 1 wherein E is nitrogen.

7. A complex as claimed in claim 1 wherein the divalent bridging group Q is selected from C(R$^{10}$)$_2$, a polyalkylene chain [C(R$^{10}$)$_2$]$_q$, a silane bridge [Si(R$^{10}$)$_2$]$_m$, or a polyalkylene-silane bridge))[C(R$^{10}$)$_2$]$_p$[Si(R$^{10}$)$_2$]$_m$, wherein the R$^{10}$ groups are independently selected from hydrogen, hydrocarbyl, substituted hydrocarbyl, heterocarbyl or nitrogen substituted heterocarbyl, m is one or more, p is one or more, and q is two or more.

8. A complex as claimed in claim 7 wherein m is 1 to 20, p is 1 to 20 and q is 2 to 20.

9. A complex as claimed in claim 1 wherein Q is selected from methylene, dimethylmethylene, ethylene, propylene, dimethylpropylene, 1,1-dimethyl-3,3-dimethylpropylene or butylene; dimethylsilyl, methylphenylsilyl, tetramethyldisiloxane, 1,1,4,4-tetramethyldisilylethylene, dimethylgermanyl, ortho, meta or para-phenylene.

10. A complex as claimed in claim 1 wherein the metal M is selected from Group IV, scandium or yttrium.

11. A complex as claimed in claim 1 wherein the metal M is selected from Ti(IV), Ti(III), Ti(II), Zr(IV), Zr(III), Zr(II), Hf(IV), Hf(III), Hf(II), Sc(III) or Y(III).

12. A complex as claimed in claim 1 wherein L is an ether, alcohol, amine, ester, phosphine, alkene, alkyne, arene, or a diene.

13. A complex as claimed in claim 1 wherein the univalent radical X is selected from C$_1$-C$_{10}$ alkyl, C$_6$-C$_{10}$ aryl, halide, hydride, hydrocarbyloxide, or amide.

14. A complex as claimed in claim 1 wherein the univalent radical X is selected from N,N-dimethylamido, N,N-diethylamido, chloro, bromo, methyl, ethyl, n-propyl, isopropyl, benzyl, n-butyl or n-octyl.

15. A complex as claimed in claim 1 having the Formula C:

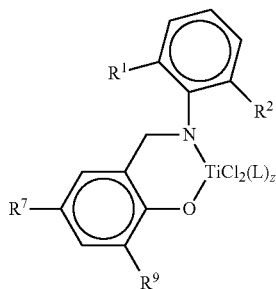

Formula (C)

wherein $R^1$ and $R^2$ are both chlorine or are both bromine, $R^7$ and $R^9$ are $C_1$ to $C_6$ alkyl, z is 1 or 2 and L is secondary amine.

16. A complex as claimed in claim 15 wherein $R^7$ and $R^9$ are tertiary butyl.

17. A catalyst for the polymerisation of 1-olefins comprising (1) the complex claimed in claim 1 and (2) an activator.

18. A catalyst as claimed in claim 17 wherein the activator is an organoaluminium compound or an organoboron compound.

19. A catalyst as claimed in claim 18 wherein the activator is an organoaluminium compound selected from trimethylaluminium, triethylaluminium, tributylaluminium, tri-n-octylaluminium, ethylaluminium dichloride, diethylaluminium chloride, methylaluminium dichloride, dimethylaluminium chloride, tris(pentafluorophenyl)aluminium or an aluminoxane.

20. A catalyst as claimed in claim 18 wherein the activator is an organo boron compound selected from dimethylphenylammonium tetraphenylborate, trityl tetraphenylborate, triphenylboron, dimethylphenylammonium tetrakis(pentafluorophenyl)borate, sodium tetrakis[(bis-3,5-trifluoromethyl)phenyl]borate, $H^+(OEt_2)_2$[(bis-3,5-trifluoromethyl)phenyl]borate, trityl tetrakis(pentafluorophenyl)borate or tris(pentafluorophenyl) boron.

21. A catalyst as claimed in claim 17 wherein the activator is a catalyst-activating support which is a solid particulate substance, insoluble in hydrocarbons, comprising at least magnesium and aluminium atoms and hydrocarbyloxy groups containing 1 to 20 carbons atoms.

22. A catalyst as claimed in claim 17 comprising the defined complex on a support material.

23. A catalyst as claimed in claim 22 wherein the support material is silica, alumina, zirconia, magnesia, magnesium chloride or a polymer or prepolymer.

24. A catalyst as claimed in claim 17 comprising more than one of the complexes.

25. A catalyst as claimed in claim 17 comprising an additional catalyst selected from a Ziegler-Natta catalyst system, a metallocene-based catalyst, or heat activated supported chromium oxide catalyst.

26. A process for the polymerisation and copolymerisation of monomeric olefins selected from 1-olefins, cycloolefins or dienes comprising contacting the monomeric olefin under polymerisation conditions with the polymerisation catalyst claimed in claim 17.

27. A process as claimed in claim 26 wherein the monomeric olefin comprises ethylene, propylene, butene, hexene, or styrene.

28. A process as claimed in claim 26 wherein the process is for copolymerisation of 1-olefin and monomers are selected from ethylene, propylene, 1-butene, 1-hexene, 4-methylpentene-1, 1-octene, methyl methacrylate, methyl acrylate, butyl acrylate, acrylonitrile, vinyl acetate, vinyl chloride, styrene, butadiene, hexadiene or norbornene.

29. A process as claimed in claim 26 wherein a monomeric olefin selected from ethylene or propylene is copolymerised with comonomer selected from 1-olefins, acrylic acid esters, vinyl esters or vinyl aromatic compounds.

30. A process as claimed in claim 29 wherein the comonomer is selected from 1-butene, 1-hexene, 4-methylpentene-1, methyl methacrylate, methyl acrylate, butyl acrylate, acrylonitrile, vinyl acetate, or styrene.

* * * * *